US00PP15217P3

(12) United States Plant Patent
Moon

(10) Patent No.: US PP15,217 P2
(45) Date of Patent: Oct. 12, 2004

(54) WILLOW OAK TREE NAMED 'QPMTF'

(50) Latin Name: *Quercus phellos*
Varietal Denomination: QPMTF

(75) Inventor: Dwayne C. Moon, County of Walton, GA (US)

(73) Assignee: Southern Selections, L.L.C., Loganville, GA (US)

( * ) Notice: Subject to any disclaimer, the term of this patent is extended or adjusted under 35 U.S.C. 154(b) by 2 days.

(21) Appl. No.: 10/294,184

(22) Filed: Nov. 13, 2002

(65) Prior Publication Data

US 2004/0093651 P1 May 13, 2004

(51) Int. Cl.[7] ..... A01H 5/00

(52) U.S. Cl. ..... Plt./225

(58) Field of Search ..... Plt./225

*Primary Examiner*—Bruce R. Campell
*Assistant Examiner*—Michelle Kizilkaya
(74) *Attorney, Agent, or Firm*—Polster, Lieder, Woodruff & Lucchesi, L.C.

(57) ABSTRACT

A Willow Oak (*Quercus phellos*) named 'QPMTF' having a dominant leader, broad spreading habit with dense canopy, fast growth rate, and spider mite resistance and also capable of being reproduced reliably from vegetative cuttings.

3 Drawing Sheets

BACKGROUND OF THE INVENTION

The present invention relates to a new and distinct variety of Willow Oak Tree (*Quercus phellos*), which I have named 'QPMTF'.

Discovery

I discovered my new tree in the spring of 1996 growing as a seedling in a production field at Moon's Tree Farm in Loganville, Walton County, Ga., among a group of cultivated Willow Oaks. These trees were grown from bare-root liners purchased in the spring of 1993 from a nursery in Florida. In the spring of 1995, these liners were relocated from my liner field to a production field. It was here that I discovered 'QPMTF'. Evaluation of this tree continued in this field until it was transplanted to an observation area adjacent to my residence at 6342 Hwy. 20, Loganville, Ga. in March of 2001.

Propagation

'QPMTF' was asexually propagated by the method of vegetative cutting at my direction in the spring of 1997. This propagation from softwood cuttings and resulting progeny has proven the characteristics of my variety to be genetically stable. Furthermore, these observations have confirmed that my new variety represents a new and improved variety of Willow Oak as particularly evidenced by the dominant leader, broad spreading habit with dense canopy, fast growth rate, and spider mite resistance, which can be reproduced by asexual propagation.

Uniqueness

'QPMTF' was discovered in a block of seedling Willow Oak purchased by Moon's Tree Farm from a supplier of liners in Florida. We claim that the genetic characteristics of this tree are the result of naturally occurring cross-pollination. Due to the nature of the seedling purchase, comparison of surrounding cross pollinators is not possible.

These improved characteristics distinguish my new tree from other typical seeding Willow Oak and the known cultivars. At the time this tree was selected, I observed 'QPMTF' Willow Oak as a 3" caliper tree exhibiting dense canopy, dominant central leader and improved spider mite resistance. The remainder of the trees in this block was 2" caliper with irregular structure and signs of spider mite damage. I assert that 'QPMTF' exhibits strong apical dominance proven by the unassisted reestablishment of a central leader after I removed the existing leader by pruning on four different occasions over a period of six years.

USE

'QPMTF' was observed for a period of several years and is believed to be particularly useful for street tree planting and in large areas such as golf courses, commercial sites and parks. 'QPMTF' will also benefit growers who will profit from a fast growing tree with consistent form and spider mite resistance.

SUMMARY OF THE INVENTION

Background

Willow Oak is typically pyramidal-shaped in youth and develops a rounded canopy at maturity. Seedlings cultivated by acorn tend to be somewhat open in youth and often lack a central leader. My new cultivar differs from the species in that it is asexually reproduced, has dominant leader, broad-spreading habit, dense canopy, fast growth rate, and spider mite resistance. Willow Oak is native to New York to Florida, west to Missouri, Oklahoma, and Texas. It thrives equally well in the heat and humidity of the Southeast and the arid Midwest. Willow Oak can be found in bottomlands and floodplains and their adjacent slopes. It prefers moist, well-drained soils in these areas but adapts readily to harsh conditions. I expect my new variety of Willow Oak to perform as well as the species.

Industry Representation

Cultivated Willow Oak is represented in the industry by seedling material reproduced by acorn. This accounts for a high degree of variability in the industry, both in the landscape and nursery. Seeding Willow Oak is variable in growth rate and habit, typically lacks a central leader, and tends to be open in youth. The only commercially available cultivar Willow Oak is *Quercus phellos* 'QPSTA' Hightower Willow Oak, U.S. Plant Pat. No. 13,677. This cultivar has a narrow pyramidal habit with a dominant central leader, dense canopy, and fast growth rate. My oak selection differs from 'QPSTA' Hightower U.S. Plant Pat. No. 13,677 in that 'QPMTF' has a broad-spreading habit. My selection in the spring of 2001 was 9¾" caliper measured at 12" above the ground with a height of 21' and a width of 17' giving it a 1.22 height to width ratio. 'QPSTA' at 9¾" caliper measured at 12" above the ground has a height of 29' and a width of 18' giving it a height to width ratio based on its patent description. This form difference, along with improved spider mite resistance, makes my selection uniquely different from all known patented selections and seedlings at time of submittal.

DESCRIPTION OF THE DRAWINGS (PHOTOGRAPHS)

The accompanying photographs which depict the color of the tree and foliage of my new variety as nearly as is reasonably possible to make the same in a color illustration of this character.

FIG. 1, taken at an observation site at 6342 Hwy. 20, Loganville, Ga. 30052 during the month of February 2002 shows the transplanted parent tree at 9 years old, 21 feet high, 17 feet wide and 9.75" in caliper. This photo depicts the winter habit of 'QPMTF' showing the dominant central leader and broad-pyramidal habit with dense branching;

FIG. 2, taken at an observation site at 6342 Hwy. 20, Loganville, Ga. 30052 during the month of August, shows the summer habit of the initially discovered tree, the broad-pyramidal habit, and the dense canopy;

FIG. 3, taken during the summer of 2001, shows the upper leaf surface of foliage on the 'QPMTF' parent tree. The absence of spider mite damage can be clearly seen;

FIG. 4 shows the lower leaf surface of foliage on the 'QPMTF' parent tree;

DETAILED DESCRIPTION

Botanical Description of the Plant

Figure 1:
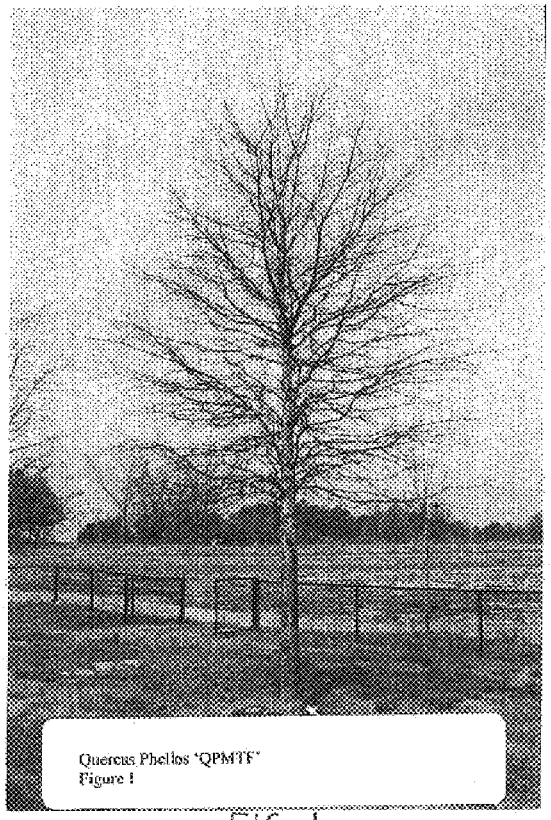
Figure 2:
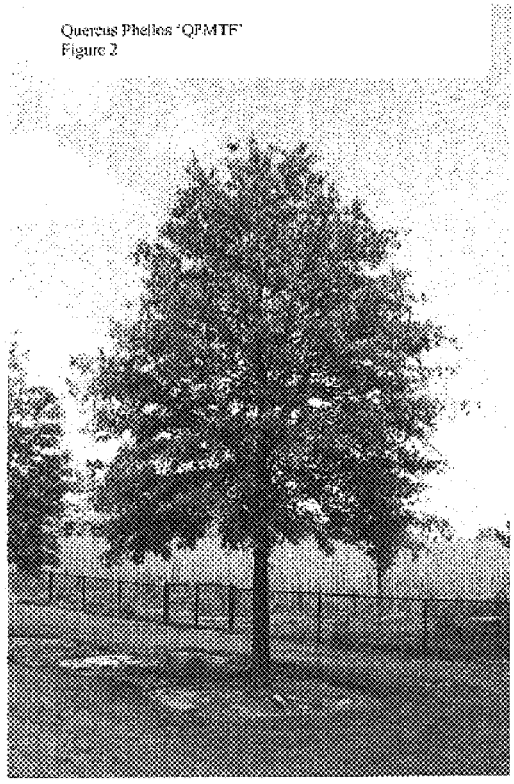
Figure 5:
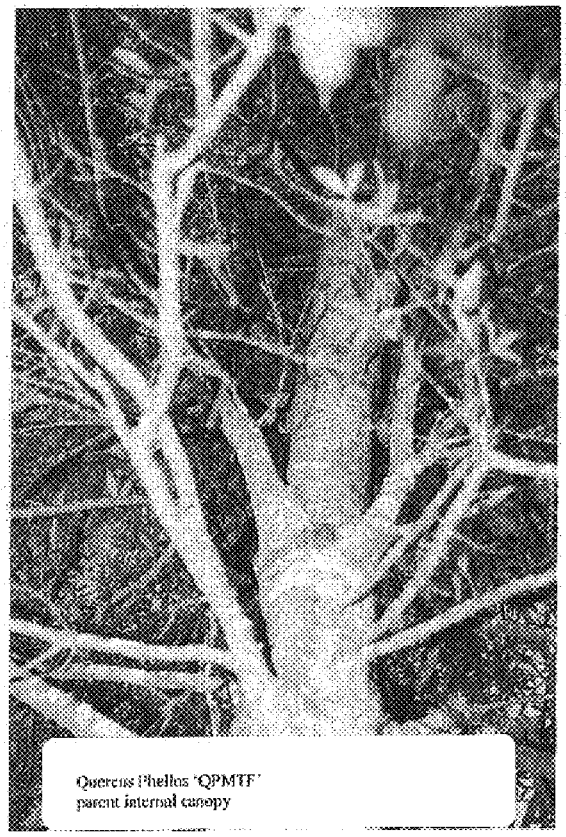
FIG. 5 shows the internal canopy of the 'QPMTF' parent tree.
Figure 6:
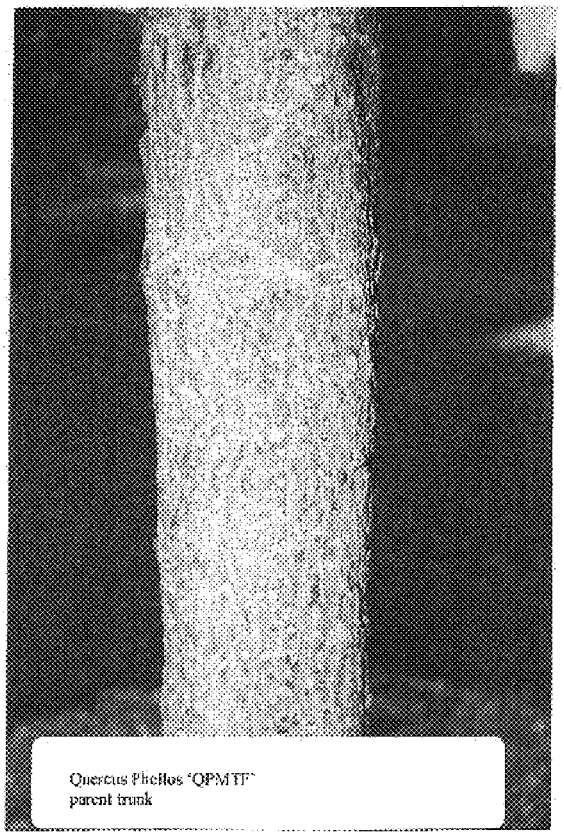
FIG. 6 shows the trunk of the 'QPMTF' parent tree.

The following is a detailed description of 'QPMTF' Willow Oak with color terminology in accordance with The Royal Horticulture Society (R.H.S.) color chart except where the context indicates a term having its ordinary dictionary meaning.

My new tree has not been observed under all growing conditions and variations may occur as a result of different growing conditions. All progeny of my new variety, insofar as have been observed, have remained genetically stable in all characteristics described hereinafter. Other than as set out hereinafter, as of this time no other characteristics have been observed which are different from common Willow Oak trees, which have been observed by the inventor.

Parentage: Seedling of *Quercus phellos* grown from bare-root liner purchased in the spring of 1993 from a nursery in Florida.

Locality where grown and observed: 'QPMTF' Willow Oak trees are currently in production at Moon's Tree Farm in Walton County, Ga. This area of Walton County has a clay loam soil type with rainfall that varies between 30" and 60" annually. This particular area is located in USDA Hardiness Zone 7.

Size and growth rate: The original tree, aged 9 years measured 9¾" in caliper at 12" above the ground. The height of 21' and spread of 17' provides a 1.22 height to width ratio. Prior to 'QPMTF' parent tree being transplanted to the observation area, the average growth rate was 1.25" per year.

Foliage: Typical of the species, alternate, simple, narrowly elliptical, tipped with a bristle, entire, 0.75" wide by 3.5; medium green above like (RHS 144A) and lighter green below like (RHS145A); fall color; typical of the species, being yellow to yellow-brown (RHS13A); petiole; brown-green ⅛" to ¼" long. Leaves exhibit a pinnate venation pattern.

Buds: Imbricate, ⅛" to ¼" long, ovoid, sharp-pointed chestnut brown (RHS200D).

Flowers: Has not yet flowered.

Fruit: Has not yet fruited.

Trunk: Typical of the species, smooth, gray, becoming gray-brown like (RHS201B) and developing irregular furrows and scales with age. At time of submittal, the trunk diameter was 9¾" measured 12" above the ground.

Branching: Slightly ascending to nearly horizontal at the base, emerging at 80–90 degrees from the trunk. Upper branches are more ascending, emerging at 30 degrees or more from the trunk. Color is gray (RHS 195B), becoming gray-brown with age.

Shade: Broad pyramidal with dense branching and dominant central leader.

Root system: More fibrous than the species which tends to have a medium to coarse root system.

Vigor: In production, the progeny have averaged 1.25" in caliper per year, which is about 25% faster than typical seedling Willow Oak. The root development from time of softwood cuttings to a finished rooted 3½" pot is five to seven weeks.

Disease: Free from disease.

Pests: Displays spider mite resistance; many Willow Oaks can develop serious mite problems that affect growth and leaf color during the summer growing season.

What is claimed is:

1. A new and distinct variety of Willow Oak tree named 'QPMTF' substantially as herein shown and described, characterized particularly as to novelty by its dominant leader, broad-spreading habit with dense canopy, fast growth rate, and spider mite resistance.

* * * * *

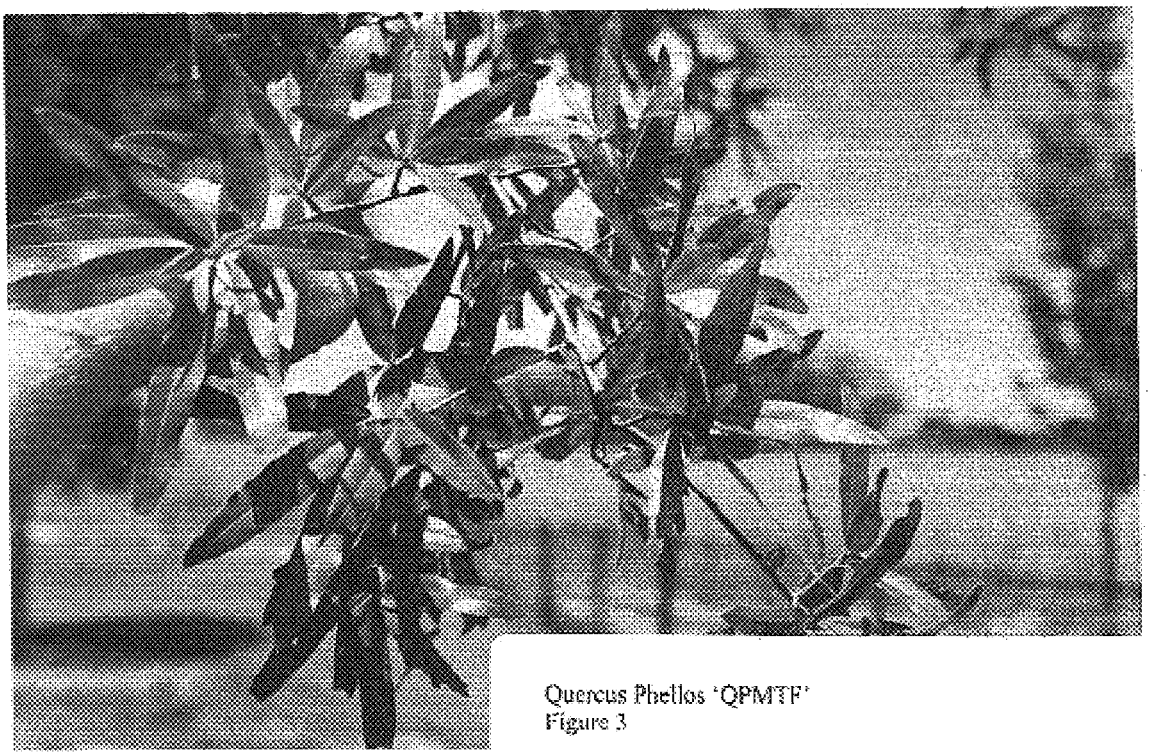
Quercus Phellos 'QPMTF'
Figure 3
FIG. 3
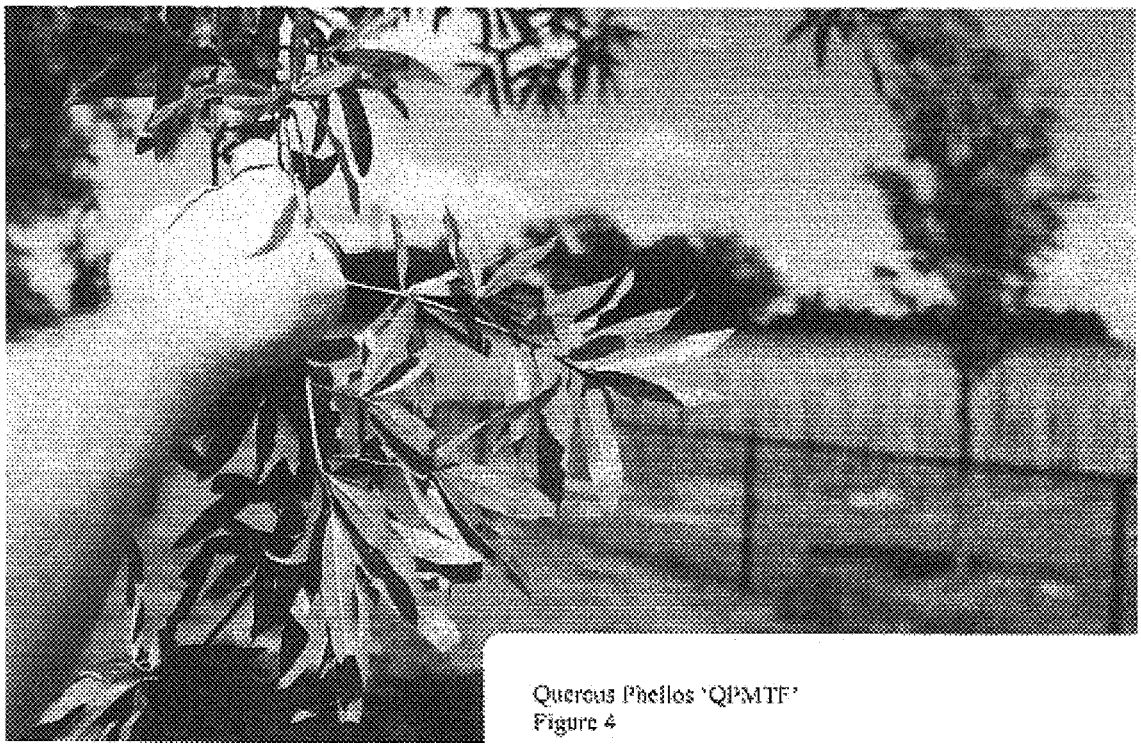
Quercus Phellos 'QPMTF'
Figure 4
FIG. 4